United States Patent
Rautenberg et al.

(10) Patent No.: US 11,014,878 B2
(45) Date of Patent: May 25, 2021

(54) METHOD FOR PREPARING 3-METHYLTHIOPROPIONALDEHYDE

(71) Applicant: Evonik Operations GmbH, Essen (DE)

(72) Inventors: Stephan Rautenberg, Bornheim (DE); Sascha Ceylan, Frankfurt (DE); Martin Koerfer, Kahl (DE); Judith Hierold, Hannover (DE); Harald Jakob, Hasselroth (DE); Christian Kaiser, Waldaschaff (DE); Rainer Malzkorn, Grosskrotzenburg (DE); Thorsten Merker, Hanau (DE); Anja Nordschild, Oberursel (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/076,247

(22) PCT Filed: Feb. 14, 2017

(86) PCT No.: PCT/EP2017/053270
§ 371 (c)(1),
(2) Date: Aug. 7, 2018

(87) PCT Pub. No.: WO2017/140665
PCT Pub. Date: Aug. 24, 2017

(65) Prior Publication Data
US 2020/0299232 A1 Sep. 24, 2020

(30) Foreign Application Priority Data
Feb. 15, 2016 (EP) .................... 16155700

(51) Int. Cl.
*C07C 319/18* (2006.01)
*C07C 319/14* (2006.01)
*C07C 323/22* (2006.01)

(52) U.S. Cl.
CPC .......... *C07C 319/18* (2013.01); *C07C 319/14* (2013.01); *C07C 323/22* (2013.01)

(58) Field of Classification Search
CPC .... C07C 319/18; C07C 319/14; C07C 323/22
See application file for complete search history.

(56) References Cited

U.S. PATENT DOCUMENTS

| 2,776,996 | A | | 1/1957 | Hunt et al. |
| 4,048,232 | A | | 9/1977 | Koberstein et al. |
| 4,225,516 | A | | 9/1980 | Biola et al. |
| 4,319,044 | A | * | 3/1982 | Matsumoto ............. B01J 31/00 562/559 |
| 5,925,794 | A | * | 7/1999 | Hsu ...................... C07C 319/18 568/41 |
| 8,759,592 | B2 | * | 6/2014 | Finkeldei ............. C07C 319/20 568/41 |

FOREIGN PATENT DOCUMENTS

| CH | 253951 | | 4/1948 |
| CH | 582 665 | A5 | 12/1976 |
| DE | 1 168 408 | | 4/1964 |
| DE | 1 618 884 | | 9/1971 |
| DE | 1 618 879 | | 12/1971 |
| JP | 4 621 609 | | 4/1966 |
| JP | S55100358 | A | 7/1980 |
| JP | 2014508730 | A | 4/2014 |
| JP | 2015521637 | A | 7/2015 |

OTHER PUBLICATIONS

International Search Report and Written Opinion dated Apr. 20, 2017, in PCT/EP2017/053270 filed Feb. 14, 2017.
Office Action received on Feb. 25, 2021, in Japanese Patent Application No. 2018-543126.
Zhurnal Vsesoyuznogo Khimicheskogo Obshchestva im. D. I. Mendeleeva,1981,26(1),108-9.

* cited by examiner

*Primary Examiner* — Rosalynd A Keys
(74) *Attorney, Agent, or Firm* — Oblon, McClelland, Maier & Neustadt, L.L.P.

(57) ABSTRACT

The present invention relates to a method for preparing 3-methylthiopropionaldehyde by reacting methyl mercaptan with acrolein, in which deviations in the stoichiometry of methyl mercaptan to acrolein in the reaction to give 3-methylthiopropionaldehyde are compensated for by supplying or by forming 1,3-bis(methylthio)-1-propanol, and also to the use of 1,3-bis(methylthio)-1-propanol as a storage form of methyl mercaptan and/or 3-methylthiopropionaldehyde.

12 Claims, No Drawings

METHOD FOR PREPARING 3-METHYLTHIOPROPIONALDEHYDE

The present invention relates to a method for preparing 3-methylthiopropionaldehyde by reacting methyl mercaptan with acrolein, in which deviations in the stoichiometry of the reactants are compensated for by supplying or by forming 1,3-bis(methylthio)-1-propanol, and also to the use of 1,3-bis(methylthio)-1-propanol as a stable storage form of methyl mercaptan and/or 3-methylthiopropionaldehyde.

3-Methylthiopropionaldehyde, also known by the abbreviation MMP for methylmercaptopropionaldehyde or by the name 4-thiapentanal (UN number 2785), is an important intermediate in the production of D,L-methionine and its hydroxy analogue 2-hydroxy-4-methylthiobutyric acid, also known by the abbreviation MHA for methionine hydroxy analogue. The preparation of 3-methylthiopropionaldehyde by reacting methyl mercaptan with acrolein is known from the prior art. It is also known from the literature that this reaction proceeds exothermically. This heat of reaction is problematic, particularly with regard to acrolein, since this compound readily undergoes radical or ionic polymerization. The 3-methylthiopropionaldehyde reaction product itself also readily undergoes side reactions which result in formation of high-boiling distillation residues. In order to be able to better control the heat of reaction in the preparation of 3-methylthiopropionaldehyde, GB 1150252 A discloses a two-stage method for preparing 3-methylthiopropionaldehyde in which methyl mercaptan is reacted with 3-methylthiopropionaldehyde in the first stage until the evolution of heat is practically complete, and the reaction product obtained in the first stage is reacted with acrolein in the second stage. According to GB 1150252 A, the reaction in the second stage is carried out using an excess of acrolein.

In the methods according to documents GB 1173174 A and GB 1166961 A, 3-methylthiopropionaldehyde is prepared in both cases by direct reaction of methyl mercaptan with acrolein. In the method according to the technical teaching of GB 1166961 A, 3-methylthiopropionaldehyde is prepared by reacting methyl mercaptan with a solution containing acrolein and water, which was obtained by condensation or by treatment with water of the reaction gases from the catalytic oxidation of propylene, in which the solution containing acrolein has a water content of less than 15 percent by weight and is free of unsaturated organic acids. In the method according to the technical teaching of GB 1166961 A, 3-methylthiopropionaldehyde is prepared by reacting acrolein with methyl mercaptan in the liquid phase at temperatures of up to 120° C., wherein the rectification of the crude 3-methylthiopropionaldehyde obtained is carried out at specific temperatures and for a specific time period. Both GB 1173174 A and GB 1166961 A teach the use of an excess of acrolein with respect to methyl mercaptan in the preparation of 3-methylthiopropionaldehyde.

Methyl mercaptan and acrolein react in an equimolar ratio to give 3-methylthiopropionaldehyde. Any deviation from this stoichiometry therefore leads either to an excess of acrolein or of methyl mercaptan. In the case of an excess of acrolein, the excess acrolein very readily undergoes polymerization. This is because acrolein can polymerize both cationically or anionically and free-radically. The polymers are also formed irreversibly and thus the polymerized acrolein cannot be recovered for a further reaction with methyl mercaptan. The use of excess acrolein in the synthesis of 3-methylthiopropionaldehyde according to the technical teaching of the documents cited above therefore has the major disadvantage that considerable amounts of the expensive acrolein starting compound are lost due to irreversible by-product formation. A further disadvantage of the prior art is that the by-products formed in the polymerization of acrolein are mainly high-boiling residues. These high boilers disrupt the subsequent preparation of methionine or MHA, e.g. during the crystallization of methionine. Therefore, the product mixture comprising 3-methylpropionaldehyde must be subjected to a vacuum distillation at high temperatures. Relatively high concentrations of high-boiling residues result in loss of products of value and they must also be disposed of which is costly. Therefore, the methods known from the prior art are not suitable for industrially economic production of methionine.

Theoretically, an excess of acrolein in the reaction mixture could be countered by addition of methyl mercaptan. However, the separation of methyl mercapatan from a mixture comprising 3-methylthiopropionaldehyde is more difficult than expected. For example, low amounts of methyl mercaptan can only be removed with difficulty from the product mixture by distillation. Consequently, corresponding amounts of the valuable starting material methyl mercaptan are wasted even in this case. More problematic, however, is that the methyl mercaptan present in the 3-methylthiopropionaldehyde outgasses during the further conversion to methionine and thereby disrupts the methionine production. In addition, outgassing of methyl mercaptan leads to a considerable odour nuisance.

Furthermore, it would also be theoretically possible to react acrolein with methyl mercaptan in the stoichiometrically required amounts to give 3-methylthiopropionaldehyde by regulating the heat of reaction released, for example. In continuously operated industrial processes, it is not possible in practice to supply stoichiometirc amounts of the reactants to the reaction in question without the substances being buffered and intermediately stored in storage vessels. The hazard potential of the substances to be stored must be offset with complex and cost-intensive constructions and safety measures.

A need therefore exists for a method for preparing 3-methylthiopriopionaldehyde from acrolein and methyl mercaptan in which, on variation in the amounts of the starting compounds acrolein and methyl mercaptan supplied, losses of methyl mercapatan and the formation of by-products due to polymerization of acrolein are avoided.

This object is achieved according to the invention in that deviations in the stoichiometry of methyl mercaptan to acrolein in the reaction of acrolein with methyl mercaptan to give 3-methylthiopropionaldehyde are compensated for by addition of the hemithioacetal 1,3-bis(methylthio)-1-propanol formed by addition of methyl mercaptan to 3-methylthiopropionaldehyde or the mixture of the hemithioacetal with 3-methylthiopropionaldehyde is used for this purpose.

The present invention therefore relates to a method for continuously preparing 3-methylthiopropionaldehyde by reacting methyl mercaptan with acrolein, characterized in that deviations in the stoichiometry of methyl mercaptan to acrolein in the reaction to give 3-methylthiopropionaldehyde are compensated for by supplying or by forming 1,3-bis(methylthio)-1-propanol, where if methyl mercaptan is present in excess with respect to acrolein, excess methyl mercaptan is converted to 1,3-bis(methylthio)-1-propanol with 3-methylthiopropionaldehyde, or if acrolein is present in excess with respect to methyl mercaptan, 1,3-bis(methylthio)-1-propanol is supplied to the reaction of methyl mercaptan with acrolein.

Deviations in the stoichiometry of methyl mercaptan to acrolein may be determined by measuring the mass flow and by determination of unreacted methyl mercaptan and acrolein in the 3-methylthiopropionaldehyde produced. In a matrix of 3-methylthiopropionaldehyde, acrolein can be determined by UV-Vis spectrometry on account of the characteristic absorption at 366 nm (by the $\alpha,\beta$-unsaturated carbonyl group). This method allows a reliable determination of acrolein with sufficient precision for acrolein concentrations of up to 0.6% in a matrix of 3-methylthiopropionaldehyde. At higher concentrations, acrolein should be determined by gas chromatography. Methyl mercaptan can be determined in a matrix of 3-methylthiopropionaldehyde by argentometric titration using potentiometric indication of the end point.

With respect to its performance the method according to the invention is not limited to one configuration form. Either a continuous, a semi-continuous or a batchwise method procedure are conceivable. However, preference is given to a continuous operating mode. This is because in a continuous operating mode, firstly acrolein and methyl mercaptan can be supplied to the method according to the invention from processes likewise operated continuously and secondly it is possible to incorporate the method into already existing or planned processes for the production of methionine. The reaction of methyl mercaptan with acrolein to give 3-methylthiopropionaldehyde can be carried out in a single reactor or in two or more reactors arranged either in parallel or in series. In a method regime operated preferably continuously, the reaction is carried out in a continuously operated stirred tank or in a flow tube. In order to achieve as far as possible complete conversions, the reaction is carried out preferably in at least two reactors arranged in series, particularly in a continuously operated stirred tank as first reactor and a flow tube as downstream reactor. In this combination, the continuously operated stirred tank serves to achieve a maximum degree of conversion and the subsequent flow tube serves to complete the reaction.

With regard to the content of acrolein and methyl mercaptan in the relevant streams supplied to the preparation of 3-methylthiopropionaldehyde, the method according to the invention is not subject to any limitations. The respective streams therefore comprise acrolein or methyl mercaptan at concentrations of 1 to 99% by weight or even more. Apart from acrolein or methyl mercaptan, the respective streams may thus also comprise by-products, as long as it is ensured that the respective acrolein and methyl mercaptan streams contain sufficient amounts such that plant shutdowns cannot occur. For example, a stream containing acrolein may also contain water and/or acetaldehyde, and a stream containing methyl mercaptan may also contain water, dimethyl sulphide and/or dimethyl ether.

In the context of the present invention, the expressions amount and amounts do not refer to flow rates but to a molar amount of the relevant component or molar amounts of the relevant components.

The reaction of methyl mercaptan with acrolein to give 3-methylthiopropionaldehyde and also the formation of 1,3-bis(methylthio)-1-propanol is followed by treating the product stream obtained from the respective reactions in a stripping step in order to remove low-boiling secondary components, followed by a distillation in which the end product is distilled off under reduced pressure as top product. The bottom product can be fed to a second distillation stage in which the high-boiling residues are further concentrated by recycling the 3-methylthiopropionaldehyde material of value.

The 1,3-bis(methylthio)-1-propanol formed in the method according to the invention or supplied to the method according to the invention is generally not only present in the form of this compound. This is because 1,3-bis(methylthio)-1-propanol is a so-called hemithioacetal or half-thioacetal which is formed in an equilibrium reaction by addition of methyl mercaptan to the carbonyl function of 3-methylthiopropionaldehyde.

In one embodiment of the method according to the invention, 1,3-bis(methylthio)-1-propanol is therefore present in equilibrium with 3-methylthiopropionaldehyde and methyl mercaptan.

However, the reaction equilibrium for the formation of 1,3-bis(methylthio)-1-propanol from 3-methylthiopropionaldehyde and methyl mercaptan lies largely on the side of 1,3-bis(methylthio)-1-propanol. Investigations have shown that, in a range from 10 to 70° C., the proportion of 1,3-bis(methylthio)-1-propanol in a corresponding equilibrium mixture is between at least 75% at 70° C. and at least 85% at 10° C. Consequently, in an equilibrium mixture of 1,3-bis(methylthio)-1-propanol, the predominant portion of the methyl mercaptan contained therein is present in bound form as part of the hemithioacetal of 3-methylthiopropionaldehyde. In contrast to methyl mercaptan which requires storage as a liquefied gas, 1,3-bis(methylthio)-1-propanol can be stored in pure form or in a mixture with other compounds, in particular with 3-methylthiopropionaldehyde, just in a simple storage vessel and under only slight positive pressure. The storage of 1,3-bis(methylthio)-1-propanol is thus significantly simpler, safer and more cost-effective than that of methyl mercaptan.

A stoichiometric reaction of anhydrous methyl mercaptan with anhydrous 3-methylthiopropionaldehyde gives a solution comprising 31.6% by weight methyl mercaptan, wherein 3-methylthiopropionaldehyde and methyl mercaptan are present in equilibrium with 1,3-bis(methylthio)-1-propanol. However, at a ratio of methyl mercaptan to 3-methylthiopropionaldehyde of greater than 1:1, the additional methyl mercaptan no longer undergoes an addition reaction to the hemithioacetal; rather the additional methyl mercaptan is now present only physically dissolved and therefore causes a high vapour pressure. High costs thereby arise for the pressure vessels required for the handling of the mixtures containing methyl mercaptan and higher losses of methyl mercaptan due to the greater amounts of methyl mercaptan present in the offgas.

By reducing the amount of methyl mercaptan in this reaction, the corresponding vapour pressure of methyl mercaptan in the resulting solution is also lowered. The disadvantages mentioned above are thereby either avoided or at least distinctly mitigated. However, the amount of compounds then circulating in the preparation of 3-methylthiopropionaldehyde increases which requires, in addition to larger apparatuses, also greater amounts of energy for heating and cooling.

It is thus desirable to convert the maximum possible amount of the methyl mercaptan supplied to the corresponding hemithioacetal of 3-methylthiopropionaldehyde and at the same time to keep the amount of purely physically dissolved methyl mercaptan in the solution obtained as low as possible. In the context of the present invention, for solutions of methyl mercaptan in 3-methylthiopropionaldehyde having a methyl mercaptan content of ca. 4.4 to ca. 31.6% by weight, this is achieved at a molar ratio of methyl mercaptan to 3-methylthiopropionaldehyde of from ca. 0.1:1 (mol/mol) to ca. 1:1 (mol/mol). For the preferred solutions of methyl mercaptan in 3-methylthiopropionaldehyde having a methyl mercaptan content of 18.8 to 31.6% by weight, this is achieved at a molar ratio of methyl mercaptan to 3-methylthiopropionaldehyde of from ca. 0.5:1 (mol/mol) to ca. 1:1 (mol/mol). And for the further preferred solutions of methyl mercaptan in 3-methylthiopropionaldehyde having a methyl mercaptan content of 27.0 to 29.3% by weight, this is achieved at a molar ratio of methyl mercaptan to 3-methylthiopropionaldehyde of from ca. 0.8:1 (mol/mol) to ca. 0.9:1 (mol/mol), based in each case on anhydrous methyl mercaptan and anhydrous 3-methylthiopropionaldehyde.

In one embodiment of the method according to the invention, the molar ratio of methyl mercaptan to 3-methylthiopropionaldehyde in the reaction to give 1,3-bis(methylthio)-1-propanol is thus from 0.1:1 (mol/mol) to 1:1 (mol/mol), particularly preferably 0.5:1 (mol/mol) to 1:1 (mol/mol) or 0.8:1 (mol/mol) to 0.9:1 (mol/mol).

In the presence of an excess of methyl mercaptan with respect to acrolein, the deviation in the stoichiometry may be compensated for by reacting the excess methyl mercaptan with 3-methylthiopropionaldehyde to give 1,3-bis(methylthio)-1-propanol. Alternatively, in the presence of an excess of acrolein with respect to methyl mercaptan, the deviation in the stoichiometry can be compensated for by supplying 1,3-bis(methylthio)-1-propanol to the reaction of methyl mercaptan with acrolein. In this variant, the acrolein in all probability does not react directly with 1,3-bis(methylthio)-1-propanol but with the equilibrium proportion of methyl mercaptan which is present in equilibrium with 1,3-bis(methylthio)-1-propanol. The methyl mercaptan is very rapidly reformed by a rapid reestablishment of the equilibrium. For the reasons stated, 1,3-bis(methylthio)-1-propanol is very suitable for the purpose of buffering acrolein by means of the conversion to 3-methylthiopropionaldehyde, e.g. during a stoppage of the production of methyl mercaptan upstream of the preparation of 3-methylthiopropionaldehyde.

Thus, in a further embodiment of the method according to the invention, excess acrolein is reacted with 1,3-bis(methylthio)-1-propanol to give 3-methylthiopropionaldehyde.

The methyl mercaptan supplied in the method according to the invention is preferably prepared by the reaction of methanol with an excess of hydrogen sulphide in the gas phase over aluminium oxide laden with an alkali metal tungstate. Further processing is carried out by steps known to those skilled in the art. In terms of the aggregate form in which methyl mercaptan is supplied to the method according to the invention, the method is not subject to any limitations. The methyl mercaptan or the stream containing methyl mercaptan in the method according to the invention can therefore be both a liquid phase and a gas phase. Compared to a stream containing gaseous methyl mercaptan, a stream containing liquid methyl mercaptan has the advantage that the mass flow can be precisely determined and the next stage of the process can be precisely regulated. Therefore, preference is given to using methyl mercaptan in the liquid phase in the method according to the invention.

The 1,3-bis(methylthio)-1-propanol required to adjust the stoichiometry in the preparation of 3-methylthiopropionaldehye is generated in the simplest case directly from the method product itself. This is carried out in a manner such that a proportion of the stream containing methyl mercaptan is not fed to the reaction with acrolein but is branched off before the reaction to give 3-methylpropionaldehyde and is supplied for the formation of 1,3-bis(methylthio)-1-propanol by reacting 3-methylpropionaldehyde with methyl mercaptan.

In an additional embodiment of the method according to the invention, therefore, a portion of the stream containing methyl mercaptan is branched off before the reaction to give 3-methylthiopropionaldehyde and is supplied for the formation of 1,3-bis(methylthio)-1-propanol by reacting 3-methylthiopropionaldehyde with methyl mercaptan.

The 1,3-bis(methylthio)-1-propanol generated in this manner may be fed to the method according to the invention in order to compensate for the variations in the stoichiometry of acrolein to methyl mercaptan in the preparation of 3-methylthiopropionaldehyde from acrolein and methyl mercaptan. For this purpose, the 1,3-bis(methylthio)-1-propanol can be intermediately stored and the intermediately stored 1,3-bis(methylthio)-1-propanol may be used to compensate for the difference between preparation and consumption of 1,3-bis(methylthio)-1-propanol.

In parallel to the diversion of a portion of the stream containing methyl mercaptan before the reaction to 3-methylthiopropionaldehyde, a stream containing 1,3-bis(methylthio)-1-propanol can in addition be supplied to the method according to the invention. This parallel process of the method according to the invention enables a rapid and precise response to deviations in the stoichiometry of methyl mercaptan to acrolein in the reaction to give 3-methylthiopropionaldehyde. In detail, the diversion of a portion of the stream containing methyl mercaptan from the method according to the invention or before the reaction to 3-methylpropionaldehyde has the advantage that a deviation in the stoichiometry of methyl mercaptan to acrolein is at least more rapidly and precisely buffered, or is even directly compensated for as it occurs, in the case of a sudden and/or briefly arising excess of supplied methyl mercaptan compared to acrolein. The supply of a stream containing 1,3-bis(methylthio)-1-propanol in the method according to the invention has the advantage that a deviation in the stoichiometry of methyl mercaptan to acrolein is counteracted directly, in the case of a sudden and/or briefly arising excess of supplied acrolein compared to methyl mercaptan, by reacting excess acrolein with supplied 1,3-bis(methylthio)-1-propanol to give 3-methylthiopropionaldehyde.

Thus, in a further embodiment of the method according to the invention, a minimum stream of methyl mercaptan is branched off before the reaction to give 3-methylthiopropionaldehyde and in parallel a minimum stream of 1,3-bis(methylthio)-1-propanol is supplied to the method according to the invention.

Preferably, the stream of methyl mercaptan branched off from the method according to the invention before the reaction to give 3-methylpropionaldehyde is supplied to the formation of 1,3-bis(methylthio)-1-propanol by reacting 3-methylpropionaldehyde with methyl mercaptan.

In the context of the present invention, a minimum stream of methyl mercaptan refers to the amount of methyl mercaptan which is technically required to maintain the reaction of methyl mercaptan with 3-methylthiopropionaldehyde.

In the context of the present invention, a minimum stream of 1,3-bis(methylthio)-1-propanol refers to the amount of 1,3-bis(methylthio)-1-propanol which is required for a rapid and precise measurement of the technically available flow control.

The intermediate storage of 1,3-bis(methylthio)-1-propanol enables the variations in the stoichiometry of acrolein with respect to methyl mercaptan in the preparation of 3-methylthiopropionaldehyde to be compensated for in a time-independent manner and according to demand. The amount of intermediately stored 1,3-bis(methylthio)-1-propanol is advantageously adapted to the deviations in the stoichiometry of methyl mercaptan with respect to acrolein. This means that the amount of intermediately stored 1,3-bis(methylthio)-1-propanol should be large enough so that, if it is supplied to the method according to the invention, the deviations in the stoichiometry, caused by the upstream plants, can be compensated for in a typical time period in the production.

Therefore, in a further embodiment of the method according to the invention, the 1,3-bis(methylthio)-1-propanol formed is intermediately stored.

Therefore, in a preferred embodiment of the method according to the invention, the molar amount of intermediately stored 1,3-bis(methylthio)-1-propanol to be supplied is at least as large as the amount of excess acrolein.

By means of the intermediately stored 1,3-bis(methylthio)-1-propanol, in particular in an amount to be supplied in the preparation of 3-methylthiopropionaldehyde which is at least as large as the excess of acrolein with respect to methyl mercaptan, it is ensured that a deviation in the stoichiometry of acrolein with respect to methyl mercaptan in the method according to the invention can be compensated for.

During a relatively long operation of 3-methylthiopropionaldehyde preparation using an excess of methyl mercaptan and feeding of 1,3-bis(methylthio)-1-propanol, the production of methyl mercaptan should be sharply increased such that either no, or only a small and/or a brief, deviation in the stoichiometry of acrolein with respect to methyl mercaptan occurs. Secondly, during a relatively long operation of 3-methylthiopropionaldehyde preparation using an excess of methyl mercaptan with simultaneous preparation of 1,3-bis(methylthio)-1-propanol, the production of methyl mercaptan should be correspondingly reduced.

Therefore, in a further preferred embodiment of the method according to the invention, if acrolein is present in excess with respect to methyl mercaptan, the intermediately stored 1,3-bis(methylthio)-1-propanol is supplied to the reaction of methyl mercaptan with acrolein and is reacted with the excess acrolein to give 3-methylthiopropionaldehyde.

If acrolein is present in excess with respect to methyl mercaptan in the preparation of 3-methylthiopropionaldehyde from acrolein and methyl mercaptan, it is essential to avoid losses of acrolein. This is because acrolein very readily polymerizes to give high-boiling residues. Since this polymerization is irreversible, the amount of polymerized acrolein is no longer available for conversion to the 3-methylthiopropionaldehyde target compound. This leads to a reduced selectivity for the formation of 3-methylthiopropionaldehyde, based on the amount of acrolein reacted. Both in the preparation of 3-methylthiopropionaldehyde and for the preparation of D,L-methionine, acrolein is the most expensive starting material. Therefore, any loss of acrolein due to formation of by-products without added value not only directly diminishes the economic efficiency of a method for preparing 3-methylthiopropionaldehyde but also in particular that of a method for preparing D,L-methionine. If acrolein is thus present in excess with respect to methyl mercaptan in the method according to the invention, 1,3-bis(methylthio)-1-propanol is therefore supplied to the method in an amount which is sufficient to convert the excess acrolein to 3-methylthiopropionaldehyde. 1,3-bis(methylthio)-1-propanol is determined by an analytical method known to those skilled in the art and suitable for this determination.

Therefore, in a preferred embodiment of the method according to the invention, the molar amount of 1,3-bis(methylthio)-1-propanol supplied is at least as large as the excess of acrolein.

If a product mixture is obtained in the method according to the invention in which unreacted 1,3-bis(methylthio)-1-propanol is present in excess, this signifies a loss of the acrolein, methyl mercaptan and 3-methylthiopropionaldehyde substances of value. Therefore, the unreacted 1,3-bis(methylthio)-1-propanol in the product mixture obtained from the method according to the invention should be reused.

Therefore, in a preferred embodiment of the method according to the invention, the unreacted 1,3-bis(methylthio)-1-propanol formed is recovered.

The recovered 1,3-bis(methylthio)-1-propanol may either be intermediately stored for a later reaction with excess acrolein to give 3-methylmercaptopropionaldehyde or alternatively be directly reacted with the excess acrolein.

In a preferred embodiment of the method according to the invention, the recovered 1,3-bis(methylthio)-1-propanol is intermediately stored.

In an alternative preferred embodiment of the method according to the invention, if acrolein is present in excess with respect to methyl mercaptan, a stream with excess acrolein is branched off before the reaction to give 3-methylthiopropionaldehyde and is reacted with the unreacted 1,3-bis(methylthio)-1-propanol separated from the product mixture to give 3-methylthiopropionaldehyde.

In another alternative preferred embodiment of the method according to the invention, equal amounts of unreacted 1,3-bis(methylthio)-1-propanol separated from the product mixture and acrolein are reacted to give 3-methylthiopropionaldehyde.

In the context of the present invention, it has been shown that the addition of a catalyst mixture of at least one nitrogen-containing base and at least one acid has a positive effect on the reaction of methyl mercaptan with acrolein to give 3-methylthiopropionaldehyde. The formation of high-boiling impurities or residues is notably reduced by addition of this catalyst mixture and at the same time the yield of the target compound is increased.

Therefore, the reaction to give 3-methylthiopropionaldehyde is preferably carried out in the presence of at least one nitrogen-containing base and at least one acid.

At a slightly acidic pH, the acrolein briefly present is the most stable. A slightly acidic pH is set most easily by the acid being present in excess with respect to the base in the preferred catalyst mixture used. Therefore, in one embodiment, the acid is present in excess with respect to the base in the catalyst mixture used.

The addition of the catalyst mixture in the reaction of methyl mercaptan with 3-methylthiopropionaldeyde to give 1,3-bis(methylthio)-1-propanol has a positive effect on the yield of the hemithioacetal and also reduces the formation of higher boiling residues.

Therefore, the formation of 1,3-bis(methylthio)-1-propanol is preferably carried out in the presence of a catalyst mixture comprising at least one nitrogen-containing base and at least one acid.

In the context of the present invention, the catalyst is a mixture of at least one base and at least one acid. Therefore, in connection with the present invention, the catalyst used according to the invention is equivalent to the catalyst mixture used. By combining a base with an acid in the catalyst mixture, good solubility of this mixture is ensured in the liquid phases present in the method according to the invention such that the catalyst mixture in the method according to the invention acts as a homogeneous catalyst. This results in high conversion rates and high selectivity for the formation of both 3-methylpropionaldehyde and 1,3-bis (methylthio)-1-propanol.

Therefore, both the reaction of methyl mercaptan with acrolein to give 3-methylthiopropionaldehyde and the formation of 1,3-bis(methylthio)-1-propanol preferably take place in the presence of a catalyst mixture comprising at least one nitrogen-containing base and at least one acid.

The base used is preferably an unsubstituted or substituted N-heterocyclic compound or an amine of the formula $NR^1R^2R^3$, where $R^1$, $R^2$ and $R^3$ are either identical or different and are each independently hydrogen, an alkyl residue having one to four carbon atoms or an arylalkyl residue having 7 to 14 carbon atoms, with the proviso that, if one of the residues $R^1$, $R^2$ or $R^3$ is hydrogen, the two other residues are not hydrogen. The nitrogen-containing base is particularly preferably pyridine or alkyl substituted pyridine, such as picoline or lutidine, a tertiary amine such as trimethylamine, triethylamine, tripropylamine, tributylamine, tridecylamine, tridodecylamine or dimethylbenzylamine. The acid is preferably a mineral acid, in particular hydrochloric acid, sulphuric acid or phosphoric acid, or an organic acid, in particular formic acid, acetic acid, propionic acid, lactic acid, succinic acid, tartaric acid, citric acid or a mixture of the acids stated above.

Therefore, the base used in the method according to the invention is preferably a substituted or unsubstituted N-heterocyclic amine and/or an amine of the formula $NR^1R^2R^3$, where $R^1$, $R^2$ and $R^3$ are either identical or different and are each independently hydrogen, an alkyl residue having one to four carbon atoms or an arylalkyl residue having 7 to 14 carbon atoms, with the proviso that, if one of the residues $R^1$, $R^2$ or $R^3$ is hydrogen, the two other residues are not hydrogen, and the acid is a mineral acid and/or an organic acid.

The base is preferably a substituted or unsubstituted N-heterocyclic amine and/or an amine according to the definition above, particularly N,N-dimethylbenzylamine and/or triethanolamine, and the acid is an organic acid, particularly formic acid, acetic acid, propionic acid, lactic acid, succinic acid, tartaric acid, citric acid or a mixture thereof.

In the method according to the invention, metal cations, and particularly heavy metal cations such as $Fe^{2+}$, favour or even catalyze the formation of high boilers from aldehydes. In addition to the at least one base and the at least one acid, the catalyst mixture therefore preferably also comprises a complexing agent. By complexing metal cations, particularly heavy metal cations, the formation of undesired high boilers is suppressed, which has a positive effect on the product purity. With regard to the complexing agents suitable for complexing metal cations, the method according to the invention is in principle not subject to any limitations. Suitable complexing agents in the context of the present invention are in principle all standard so-called polydentate complexing agents, that is all complexing agents having more than one functional group suitable for complex formation such as a hydroxyl, amino or carboxyl group. In the simplest case, the complexing agent is an organic acid having more than one carboxyl group. The catalyst mixture used is therefore preferably a nitrogen-containing base in combination with at least one acid, with the proviso that the at least one acid is a complexing organic acid. In the context of the present invention, the organic acid suitable for complex formation is preferably an organic acid suitable for complexing metal ions such as $Fe^{2+}$, in particular tartaric acid.

The catalyst mixture used in the method according to the invention therefore preferably comprises at least one complexing organic acid.

As already explained above, 1,3-bis(methylthio)-1-propanol is formed in an equilibrium reaction of 3-methylthiopropionaldehyde and methyl mercaptan, wherein the equilibrium of this reaction lies largely on the side of 1,3-bis(methylthio)-1-propanol at temperatures of between 10 and 70° C. Thus, the predominant portion of the methyl mercaptan contained therein is present in bound form as part of the hemithioacetal of 3-methylthiopropionaldehyde. The lesser proportion of the methyl mercaptan present in unbound form is present in physically dissolved form in the product mixture of the formation of 1,3-bis(methylthio)-1-propanol. The NMR-spectra of product mixtures which had been stored for one or seven days show mainly the relevant signals for 1,3-bis(methylthio)-1-propanol (MMP-MC), 3-methylthiopropionaldehyde (MMP) and methyl mercaptan (MC). By-products are only observed in traces—if at all—in these NMR spectra. By reacting with acrolein, the methyl mercaptan present in bound form in 1,3-bis(methylthio)-1-propanol is released again and reacts with the acrolein to form 3-methylthiopropionaldehyde. In detail, the acrolein reacts with the equilibrium proportion of the methyl mercaptan present in unbound form. The "free" methyl mercaptan reacted is continuously reformed from the equilibrium reaction. In the reaction of one mole of 1,3-bis (methylthio)-1-propanol with one mole of acrolein, two moles of 3-methylthiopropionaldehyde are formed. Consequently, 1,3-bis(methylthio)-1-propanol is suitable for storage of both methyl mercaptan and 3-methylthiopropionaldehyde.

The present invention therefore also relates to the use of 1,3-bis(methylthio)-1-propanol as a storage form of methyl mercaptan and/or 3-methylthiopropionaldehyde.

Preferably, the storage form of methyl Mercaptan and/or 3-methylthiopropionaldehyde in the use according to the present invention is a stable storage form, wherein in the context of the present invention, a stable storage form of methyl mercaptan and/or 3-methylthiopropionaldehyde is understood to mean a corresponding storage form in which methyl mercaptan and 3-methylthiopropionaldehyde can be stored for at least 7 days without (appreciable) formation of by-products.

The 1,3-bis(methylthio)-1-propanol used as a storage form for methyl mercaptan and/or 3-methylthiopropionaldehyde arises in the simplest case from the method according to the invention for preparing 3-methylthiopropionaldehyde in which, in the case of an excess of methyl mercaptan with respect to acrolein, the excess methyl mercaptan is reacted with 3-methylthiopropionaldehyde to give 1,3-bis (methylthio)-1-propanol. Alternatively or in addition, the 1,3-bis(methylthio)-1-propanol used as a storage form for methyl mercaptan and/or 3-methylthiopropionaldehyde can also be supplied to the method according to the invention for preparing 3-methylthiopropionaldehyde, if in this method acrolein is present in excess with respect to methyl mercaptan. This is because the excess acrolein is reacted with the amount of methyl mercaptan being present in the equilibrium with 1,3-bis(methylthio)-1-propanol to give 3-methylthiopropionaldehyde.

Therefore, in one embodiment of the method according to the invention, the 1,3-bis(methylthio)-1-propanol originates from the method according to the invention for preparing 3-methylthiopropionaldehyde and/or the 1,3-bis(methylthio)-1-propanol is supplied to the method according to the invention for preparing 3-methylthiopropionaldehyde.

The present invention is further by the following items:
1. Method for preparing 3-methylthiopropionaldehyde by reacting methyl mercaptan with acrolein, characterized in that deviations in the stoichiometry of methyl mercaptan to acrolein in the reaction to give 3-methylthiopropionaldehyde are compensated for by supplying or by forming 1,3-bis(methylthio)-1-propanol,
where
if methyl mercaptan is present in excess with respect to acrolein, excess methyl mercaptan is converted to 1,3-bis(methylthio)-1-propanol with 3-methylthiopropionaldehyde,
or
if acrolein is present in excess with respect to methyl mercaptan, 1,3-bis(methylthio)-1-propanol is supplied to the reaction of methyl mercaptan with acrolein.
2. Method according to item 1, wherein the preparation is continuously performed.
3. Method according to item 1 or 2, wherein the molar ratio of methyl mercaptan to 3-methylthiopropionaldehyde in the reaction to give 1,3-bis(methylthio)-1-propanol is from 0.1:1 (mol/mol) to 1:1 (mol/mol).
4. Method according to any of items 1 to 3, wherein the excess acrolein is reacted with 1,3-bis(methylthio)-1-propanol to give 3-methylthiopropionaldehyde.
5. Method according to any of items 1 to 4, wherein a portion of the stream containing methyl mercaptan is branched off before the reaction to give 3-methylthiopropionaldehyde and is supplied to the formation of 1,3-bis(methylthio)-1-propanol by reacting 3-methylthiopropionaldehyde with methyl mercaptan.
6. Method according to any of items 1 to 5, wherein a minimum stream of methyl mercaptan is branched off before the reaction to give 3-methylthiopropionaldehyde and in parallel a minimum stream of 1,3-bis(methylthio)-1-propanol is supplied to the method according to the invention.
7. Method according to any of items 1 to 6, wherein the 1,3-bis(methylthio)-1-propanol formed is intermediately stored.
8. Method according to item 7, wherein the molar amount of intermediately stored 1,3-bis(methylthio)-1-propanol to be supplied is at least as large as the amount of excess acrolein.
9. Method according to item 7 or 8, wherein, if acrolein is present in excess with respect to methyl mercaptan, the intermediately stored 1,3-bis(methylthio)-1-propanol is supplied to the reaction of methyl mercaptan with acrolein and is reacted with the excess acrolein to give 3-methylthiopropionaldehyde.
10. Method according to any of items 1 to 9, wherein the molar amount of 1,3-bis(methylthio)-1-propanol supplied is at least as large as the excess of acrolein.
11. Method according to item 9 or 10, wherein unreacted 1,3-bis(methylthio)-1-propanol is recovered.
12. Method according to item 11, wherein the 1,3-bis(methylthio)-1-propanol recovered is intermediately stored.
13. Method according to item 11, wherein, if acrolein is present in excess with respect to methyl mercaptan, a stream with excess acrolein is branched off before the reaction to give 3-methylthiopropionaldehyde and is reacted with the unreacted 1,3-bis(methylthio)-1-propanol separated from the product mixture to give 3-methylthiopropionaldehyde.
14. Method according to item 11, wherein equal amounts of unreacted 1,3-bis(methylthio)-1-propanol separated from the product mixture and acrolein are reacted to give 3-methylthiopropionaldehyde.
15. Use of 1,3-bis(methylthio)-1-propanol as a storage form of methyl mercaptan and/or 3-methylthiopropionaldehyde.
16. Use according to item 15, wherein the storage form is a stable storage form, wherein a stable storage form of methyl mercaptan and/or 3-methylthiopropionaldehyde is a storage form in which methyl mercaptan and 3-methylthiopropionaldehyde can be stored for at least 7 days without formation of by-products.
17. Use according to item 15 or 16, wherein the 1,3-bis(methylthio)-1-propanol originates from the method according to any of items 1 to 14, and/or the 1,3-bis(methylthio)-1-propanol is supplied to the method according to any of items 1 to 14.

EXAMPLES

A. Methods Used

1. Determination of Methyl Mercaptan by Argentometric Titration

Chemicals used:
2-propanol (technical grade)
sodium acetate in ethanol (0.1 mol/l), Bernd Kraft, Cat. No. 16590.3700
silver nitrate standard solution (0.1 mol/l), Sigma-Aldrich, Cat. No. 35375
nitrogen
Alternatively, reagents from other manufacturers with comparable quality may also be used.

Equipment used:
Titrando 907, Metrohm, Cat. No. 2.907.0020
Dosino 800, Metrohm, Cat. No. 2.800.0020
Tiamo™ (titration software), Metrohm, Cat. No. 6.6056.221
Ag Titrode with sulphide coating, Metrohm, Cat. No. 6.0430.100S, with 854 iConnect, Metrohm, Cat. No. 1.854.0010
titration vessel (150 ml), Metrohm, Cat. No. 6.1415.250, with lid having 5 openings, Metrohm, Cat. No. 6.1414.010
retaining ring for titration vessel, Metrohm, Cat. No. 6.2036.000
magnetic stirrer 801 with stand, Metrohm, Cat. No. 2.801.0040
magnetic stirrer bars (length 25 mm), Metrohm, Cat. No. 6.1903.030
magnetic stirrer bar remover
glass beaker
wash bottle
disposable syringes (1 ml), Luer
disposable cannulae (70 ml), Luer
analytical balance
Alternatively, other equipment configurations from other suppliers with comparable performance characteristics may also be used.

The titration vessel was initially charged with 80 ml of a sodium acetate solution in ethanol (0.1 mol/l). Nitrogen was slowly introduced into the precharged sodium acetate solution for approx. one minute. During the sparging of the sodium acetate solution, 0.2 ml of the methyl mercaptan sample to be determined were withdrawn from the sample flask using a disposable syringe and a disposable cannula. The weight of the syringe filled with the sample was determined with an analytical balance. After terminating the nitrogen supply, the sample was added in the titration vessel and the exact amount of sample was determined by re-weighing. The titration was conducted using silver nitrate standard solution (0.1 mol/l) and the endpoint was determined by means of the Ag Titrode with sulphide coating.

If the sample contains no hydrogen sulphide in addition to the methyl mercaptan to be determined, the titration curve has only one inflection point in a range of potential between −100 and +100 mV. The methyl mercaptan content in the sample solution (in % by weight) is given by the formula:

$$MC \text{ content} = \frac{V(\text{standard solution}) * c(\text{standard solution}) * \text{molar weight }(MC) * 100}{\text{sample weight}}$$

During the titration a yellow precipitate of silver methyl mercaptide precipitated out. In samples which also contained hydrogen sulphide in addition to methyl mercaptan, the presence of hydrogen sulphide was indicated by a black precipitate of silver sulphide on addition of silver nitrate. In this case, the titration curve showed an inflection point in a range of potential between +250 and +4550 mV. The methyl mercaptan and hydrogen sulphide content in the sample (in % by weight) is given by the following formula:

$$MC \text{ content} = \frac{V(\text{std.sol.}, 2.WP) - V(\text{std.sol.}, 1.WP) * c(\text{std.sol.}) * \text{molar wt.}(MC) * 100}{\text{sample weight}}$$

$$H2S \text{ content} = \frac{V(\text{std.sol.}, 1.WP) * (\text{std.sol.}) * \text{molar weight }(H2S) * 100}{\text{sample weight} * 2}$$

Std. sol., 2. WP. and std. sol., 1. WP signify the volume (in ml) of the silver nitrate standard solution (concentration given in mol/l) consumed which was required to reach the second or first inflection point in the titration curve. The sample weight was in g and the molar weight was inserted in g/mol.

2. Determination of Acrolein in 3-Methylthiopropionaldehyde by Photometry
   Chemicals used:
   demineralized water
   Equipment used:
   UV-Vis photometer of the type UV-1202 from Shimadzu
   UV-Vis cuvettes with a path length of 10 mm
   transfer pipettes
   Alternatively, other equipment configurations from other suppliers with comparable performance characteristics may also be used.

Before the actual determination of acrolein in 3-methyl-thiopropionaldehyde, a calibration against water was firstly carried out. For this purpose, the UV-Vis cuvette was filled with demineralized water and the blank sample thus obtained was measured photometrically. Subsequently, another UV-Vis cuvette was first conditioned by at least one-time rinsing with 3-methylthiopropionaldehyde. About 1 ml of the sample to be investigated was then placed in the UV-Vis cuvette, using the transfer pipette, which was sealed and measured photometrically (at a wavelength of 366 nm). To determine the acrolein content in the sample, the absorption measured by the UV-Vis photometer was multiplied by a factor of 0.5220. The acrolein content from the UV-Vis photometer was then stated in % with a precision of three decimal places. Using this method, concentrations of up to about 0.6% acrolein in a matrix comprising 3-methylthio-propionaldehyde can be determined with sufficient precision.

3. Determination of N,N-Dimethylbenzylamine (DMBA) in 3-Methylthiopropionaldehyde by Titration
   Chemicals used:
   electrolyte solution for Ag/AgCl reference system c(KCl)=3 mol/l (250 ml), Metrohm, Cat. No. 6.2308.020
   storage solution for combined pH glass electrodes with reference electrolyte c(KCL)=3 ml, Metrohm, Cat. No. 6.2323.000
   buffer solution pH 4.00 (25° C.) in disposable portion sachet, Metrohm, Cat. No. 6.2307.200
   buffer solution pH 7.00 (25° C.) in disposable portion sachet, Metrohm, Cat. No. 6.2307.210
   buffer solution pH 9.00 (25° C.) in disposable portion sachet, Metrohm, Cat. No. 6.2307.220
   perchloric acid in glacial acetic acid (0.01 mol/l), Bernd Kraft, Cat. No. 05101.3700
   glacial acetic acid (ReagentPlus®), Sigma-Aldrich, Cat. No. A6283
   2-propanol (Chromasolv®), Sigma-Aldrich, Cat. No. 34863
   LiCl solution, saturated in ethanol
   Alternatively, chemicals from other manufacturers with comparable quality may also be used.
   Equipment used:
   Titrando 907 potentiometric titrator, Metrohm, Cat. No. 2.907.0020
   Dosino 800 metering system, Metrohm, Cat. No. 2.800.0020
   Tiamo™ (titration software), Metrohm, Cat. No. 6.6056.221
   Dosing Unit 10 ml metering unit, Metrohm, Cat. No. 6.3032.210
   Dosing Unit 50 ml metering unit, Metrohm, Cat. No. 6.3032.250
   Solvotrode electrodes for titration in non-aqueous media, Metrohm, Cat. No. 6.0229.100
   titration vessel (150 ml), Metrohm, Cat. No. 6.1415.250, with lid having 5 openings, Metrohm, Cat. No. 6.1414.010
   retaining ring for titration vessel, Metrohm, Cat. No. 6.2036.000
   magnetic stirrer 801 with stand, Metrohm, Cat. No. 2.801.0040
   magnetic stirrer bars (length 25 mm), Metrohm, Cat. No. 6.1903.030
   magnetic stirrer bar remover
   glass beaker
   wash bottle
   disposable syringes (1 ml), Luer
   disposable cannulae (70 ml), Luer
   analytical balance
   Alternatively, another equipment configuration with comparable performance characteristics may also be used.

Prior to the first measurement, the pH electrode was calibrated with buffer solutions at a pH of 4, 7 or 9 in each case. Subsequently, DMBA in MMP was determined by potentiometric titration. A plastic beaker was filled with ca. 50 ml of glacial acetic acid, ca. 50 g of sample were then added, wherein the exact amount of sample was determined by weighing. The titration was carried out using perchloric acid in glacial acetic acid (0.01 mol/l), the end point being detected by means of an electrode for titration in non-aqueous media, e.g. Solvotrode, Metrohm.

$$\text{DMBA content in MC [wt.-\%]} = \frac{V(\text{std.sol., ml}) * c\left(\text{std.sol., } \frac{\text{mol}}{l}\right) * M\left(DMBA, \frac{g}{\text{mol}}\right)}{m(\text{sample, g})}$$

V. (std. sol., ml) corresponds to the volume of perchloric acid standard solution consumed in ml.

c (std. sol., mol/l) corresponds to the concentration of perchloric acid standard solution in mol/l.

M (DMBA, g/mol) corresponds to the molar mass of the DMBA (N,N-dimethylbenzylamine) to be determined in g/mol.

m (sample, g) corresponds to the weight of the sample in g.

4. Residue Determination Using a Vacuum Distillation Unit

The determination of the residue is carried out in a vacuum distillation unit (e.g. Kugelrohr ("ball tube") evaporator, Büchi, GKR-50)

To determine the container empty weight, the vessel for the substance to be distilled was weighed. Subsequently, 15 g of the liquid to be distilled were weighed into the container and the distillation unit was assembled. The pressure regulator of the vacuum pump was set to a pressure of 30 mbar. The heating of the distillation container was set to a temperature of 200° C. After a period of 20 minutes, the distillation was terminated. After cooling the distillation unit, the apparatus was vented, the vacuum pump was switched off and the glass parts were disassembled. The distillation container was weighed and the residue determined with the aid of the formula below:

$$\text{Residue [wt.-\%]} = \frac{m(\text{contained, after dist.}) - m(\text{container, empty})}{m(\text{container, before dist.})}$$

5. Gas Chromatography

The gas chromatographic investigations were carried out using a gas chromatograph of the HP 6890 type from Agilent, which was equipped with a 19091J-213 HP-5 5% phenylmethylsiloxane capillary column from Agilent and a flame ionization detector. The analysis was conducted using a temperature gradient from 40 to 325° C. at a temperature rate of 15° C. per minute.

In the context of the present invention, gas chromatography—in addition to other methods—was used for the determination of 3-methylthiopropionaldehyde, methyl mercaptan and acrolein. The 1,3-bis(methylthio)-1-propanol formed from 3-methylthiopropionaldehyde and methyl mercaptan was unstable at the temperatures applied in the gas chromatography and therefore already decomposed into the starting compounds 3-methylthiopropionaldehyde and methyl mercaptan prior to detection.

B. Experiments 1 to 4:

25.16 g of stripped 3-methylthiopropionaldehyde (methylmercaptopropionaldehyde MMP) (93.19% by weight) from industrial production were initially charged in a flask and heated using a water bath. The amount of methyl mercaptan (MC) (12.41 ml, 11.09 g) required for the formation of 1,3-bis(methylthio)-1-propanol (MMP-MC) was charged in a cooled dropping funnel. 0.027 g or 0.095 g of a catalyst mixture composed of N,N-dimethylbenzylamine (5.2% by weight based on the catalyst), acetic acid, tartaric acid and water were added to the MMP of experiments 2 and 4. The methyl mercaptan was added dropwise via the dropping funnel to the 3-methylthiopropionaldehyde over a period of ca. 7 to 10.5 minutes such that a temperature of ca. 25° C. (experiments 1 and 2) or ca. 40° C. (experiments 3 and 4) was not substantially exceeded. Subsequently, the resulting product mixture was stirred for 15 minutes at 25° C. (experiments 1 and 2) or at 40° C. (experiments 3 and 4).

Next, the resulting product mixtures overlayed with nitrogen were stored in a flask for 1 day or 7 days at 15° C. In the NMR spectra of the product mixtures, the signals corresponding to MMP-MC, MMP and MC are primarily observed. By-products are at most observed in traces.

C. Experiments 5 to 12:

A sufficient amount of MMP (industrially produced, 93.19% by weight) was initially charged in a flask. 10.43 g (94.91% by weight) of the MMP-MC prepared in experiments 1 to 4 and stored one day or 7 days and 3.76 g (96.97% by weight) of acrolein were added dropwise from dropping funnels to the MMP over a period of ca. 7.5 minutes such that a temperature of ca. 60° C. in the liquid phase in the flask was not exceeded. The addition of catalyst was carried out according to the figures in the table below. The product mixtures were then stirred at 60° C. for 60 minutes.

The MMP-MC used in experiment 5 was prepared at 25° C. and stored for one day at 15° C. The addition of catalyst was carried out in the second step (preparation of MMP from MMP-MC and AC).

The MMP-MC used in experiment 6 was prepared at 25° C. and stored for seven days at 15° C. The addition of catalyst was carried out in the second step (preparation of MMP from MMP-MC and AC).

The MMP-MC used in experiment 7 was prepared at 25° C. and stored for one day at 15° C. The addition of catalyst was carried out in the first step (preparation of MMP-MC from MMP and MC).

The MMP-MC used in experiment 8 was prepared at 25° C. and stored for seven days at 15° C. The addition of catalyst was carried out in the first step (preparation of MMP-MC from MMP and MC).

The MMP-MC used in experiment 9 was prepared at 40° C. and stored for one day at 15° C. The addition of catalyst was carried out in the second step (preparation of MMP from MMP-MC and AC).

The MMP-MC used in experiment 10 was prepared at 40° C. and stored for seven days at 15° C. The addition of catalyst was carried out in the first step (preparation of MMP-MC from MMP and MC).

The MMP-MC used in experiment 11 was prepared at 40° C. and stored for one day at 15° C. The addition of catalyst was carried out in the first step (preparation of MMP-MC from MMP and MC).

The MMP-MC used in experiment 12 was prepared at 40° C. and stored for seven days at 15° C. The addition of catalyst was carried out in the first step (preparation of MMP-MC from MMP and MC).

The catalyst mixture contained 5.2% by weight N,N-dimethylbenzylamine.

TABLE 1

Overview of experiments 1 to 12.

| | Reactants | | | DMBA | | |
|---|---|---|---|---|---|---|
| Experiment | MMP/MC | MMP-MC/AC | Storage [d] | in sol. [ppm] | Cat. [g] | Residue [% by wt.] |
| 1 | 1/1 | — | — | 89 | — | 0 |
| 2 | 1/1.08 | — | — | 129 | 0.027 | 0 |
| 3 | 1/1.04 | — | — | 92 | — | 0.01 |
| 4 | 1/1.06 | — | — | 232 | 0.095 | 0.01 |
| 5 | — | 1/0.91 | 1 | 143 | 0.026 | 0.1 |
| 6 | — | 1/1.05 | 7 | 147 | 0.026 | 0.08 |
| 7 | — | 1/1.03 | 1 | 113 | — | 0.13 |
| 8 | — | 1/1.03 | 7 | 113 | — | 0.05 |
| 9 | — | 1/1.02 | 1 | 150 | 0.028 | 0.01 |
| 10 | — | 1/1.03 | 7 | 151 | 0.028 | 0.01 |
| 11 | — | 1/1.03 | 1 | 151 | — | 0.01 |
| 12 | — | 1/1 | 7 | 149 | — | 0.03 |

With a test sample of ca. 100 mg (experiments 5 to 12), gas chromatograms of the respective product mixtures were generated—using n-dodecane as internal intensity standard. The results of the analysis are compiled in the following table:

TABLE 2

Overview of the analyses of experiments 5 to 12.

| | GC [wt %] | | |
|---|---|---|---|
| Experiment | MMP | MC | AC |
| 5 | 92.42 | 0.50 | — |
| 6 | 94.66 | 0.03 | — |
| 7 | 93.88 | 0.15 | — |
| 8 | 93.90 | 0.12 | — |
| 9 | 94.11 | 0.16 | — |
| 10 | 95.67 | 0.14 | — |
| 11 | 94.55 | 0.02 | — |
| 12 | 94.60 | 0.04 | — |

In addition, 15 g of each product mixture were distilled using the Kugelrohr distilling bulb. Here, a brown film of 0.01 to 0.03% by weight remained on the flask wall which was determined as the dimer of MMP.

The experiments show that independently of whether the MMP-MC was prepared at 25 or 40° C., whether it was stored for one day or seven days, and independently of whether the catalyst was added to the MMP-MC or to the MMP preparation, there was no influence on the formation of high-boiling residues.

D. Experiment 13:

90 units by weight of MMP were initially charged in a reactor and then 100 units by weight of acrolein (95.7%) were introduced per hour over a period of 24 hours. Simultaneously, 83.5 units by weight of methyl mercaptan (96.1%) were introduced per hour over a period of 24 hours. In addition, 0.02 units by weight of N,N-dimethylbenzylamine, dissolved in an excess of acetic acid, were added per hour. To compensate for the excess of methyl mercaptan, 28.5 units by weight of a solution of MMP/MMP-MC comprising 7 percent by weight methyl mercaptan were introduced. The temperature was maintained at 60° C. The amount of MMP which caused an increase in the fill level in the reactor was discharged. This amount was pumped into a residence time reactor with a residence time of 0.5 hours and again discharged accordingly. The reaction solution was freed of low-boiling by-products of the acrolein and methyl mercaptan preparation in a stripping column.

Analysis of the reaction solution thus obtained revealed that 206.1 units by weight of MMP were obtained per hour. A sample of the reaction mixture was concentrated to constant weight at 220° C. and 30 mbar. A non-evaporable residue of 0.3% by weight remained. Determination of the MMP concentration revealed a content of 97.1%. This corresponds to a yield of more than 98%.

The invention claimed is:

1. A method for continuously preparing 3-methylthiopropionaldehyde, the method comprising:
   reacting methyl mercaptan with acrolein to obtain the 3-methylthiopropionaldehyde,
   wherein deviations in a stoichiometry of the methyl mercaptan to the acrolein during the reacting to obtain the 3-methylthiopropionaldehyde are compensated for by supplying or forming 1,3-bis(methylthio)-1-propanol, and
   wherein:
   if the methyl mercaptan is present in excess with respect to the acrolein, an excess methyl mercaptan is converted to the 1,3-bis(methylthio)-1-propanol with the 3-methylthiopropionaldehyde, wherein the 1,3-bis(methylthio)-1-propanol formed is intermediately stored,
   or
   if the acrolein is present in excess with respect to the methyl mercaptan, the 1,3-bis(methylthio)-1-propanol is supplied to the reacting of the methyl mercaptan with the acrolein, wherein a molar amount of intermediately stored 1,3-bis(methylthio)-1-propanol to be supplied is at least as large as an amount of an excess acrolein.

2. The method according to claim 1, wherein a molar ratio of the methyl mercaptan to the 3-methylthiopropionaldehyde during the reacting to obtain the 1,3-bis(methylthio)-1-propanol is from 0.1:1 (mol/mol) to 1:1 (mol/mol).

3. The method according to claim 1, wherein an excess acrolein is present and the excess acrolein is reacted with the 1,3-bis(methylthio)-1-propanol to obtain the 3-methylthiopropionaldehyde.

4. The method according to claim 1, wherein a portion of a stream comprising the methyl mercaptan is branched off before the reacting to obtain the 3-methylthiopropionaldehyde and is supplied to the forming of the 1,3-bis(methylthio)-1-propanol by reacting the 3-methylthiopropionaldehyde with the methyl mercaptan.

5. The method according to claim 1, wherein a minimum stream of the methyl mercaptan is branched off before reacting to obtain the 3-methylthiopropionaldehyde and
   in parallel, a minimum stream of the 1,3-bis(methylthio)-1-propanol is supplied to the reacting of the methyl mercaptan with the acrolein.

6. The method according to claim 1, wherein, if the acrolein is present in excess with respect to the methyl mercaptan, intermediately stored 1,3-bis(methylthio)-1-propanol is supplied to the reacting of the methyl mercaptan with the acrolein and is reacted with an excess acrolein to obtain the 3-methylthiopropionaldehyde.

7. The method according to claim 1, wherein a molar amount of 1,3-bis(methylthio)-1-propanol supplied is at least as large as an amount of an excess acrolein.

8. The method according to claim 6, wherein unreacted 1,3-bis(methylthio)-1-propanol is recovered.

9. The method according to claim 8, wherein the 1,3-bis(methylthio)-1-propanol recovered is intermediately stored.

10. The method according to claim 8, wherein, if the acrolein is present in excess with respect to the methyl mercaptan, a stream with an excess acrolein is branched off before the reacting to obtain the 3-methylthiopropionaldehyde and is reacted with the unreacted 1,3-bis(methylthio)-1-propanol separated from a product mixture to obtain the 3-methylthiopropionaldehyde.

11. The method according to claim 8, wherein equal amounts of the unreacted 1,3-bis(methylthio)-1-propanol separated from a product mixture and the acrolein are reacted to obtain the 3-methylthiopropionaldhyde.

12. A method for storing methyl mercaptan and/or 3-methylthiopropionaldehyde, the method comprising:
  storing the methyl mercaptan and/or 3-methylthiopropionaldehyde in form of 1,3-bis(methylthio)-1-propanol,
  wherein the 1,3-bis(methylthio)-1-propanol originates from and/or is supplied to a process for continuously preparing the 3-methylthiopropionaldehyde,
  wherein the process comprises:
  reacting methyl mercaptan with acrolein to obtain the 3-methylthiopropionaldehyde,
  wherein deviations in the stoichiometry of the methyl mercaptan to the acrolein in the reacting to obtain the 3-methylthiopropionaldehyde are compensated for by supplying or forming the 1,3-bis(methylthio)-1-propanol, and wherein:

if the methyl mercaptan is present in excess with respect to the acrolein, an excess methyl mercaptan is converted to the 1,3-bis(methylthio)-1-propanol with the 3-methylthiopropionaldehyde, wherein the 1,3-bis(methylthio)-1-propanol formed is intermediately stored, or if the acrolein is present in excess with respect to the methyl mercaptan, the 1,3-bis(methylthio)-1-propanol is supplied during the reacting of the methyl mercaptan with the acrolein, wherein a molar amount of intermediately stored 1,3-bis(methylthio)-1-propanol to be supplied is at least as large as an amount of excess acrolein.

* * * * *